(12) United States Patent
Lee et al.

(10) Patent No.: US 11,446,459 B2
(45) Date of Patent: Sep. 20, 2022

(54) RESPIRATOR FIXING MODULE

(71) Applicant: GaleMed Corporation, Yilan County (TW)

(72) Inventors: Gary C. J. Lee, Yilan County (TW); Thomas C. Loescher, Rancho Santa Fe, CA (US); Yu-Chien Yen, Yilan County (TW)

(73) Assignee: GALEMED CORPORATION, Yilan County (TW)

( * ) Notice: Subject to any disclaimer, the term of this patent is extended or adjusted under 35 U.S.C. 154(b) by 755 days.

(21) Appl. No.: 16/410,994

(22) Filed: May 13, 2019

(65) Prior Publication Data

US 2020/0261679 A1    Aug. 20, 2020

(30) Foreign Application Priority Data

Feb. 20, 2019    (TW) .................................. 108105695

(51) Int. Cl.
*A61M 16/06*    (2006.01)

(52) U.S. Cl.
CPC .... *A61M 16/0605* (2014.02); *A61M 16/0666* (2013.01); *A61M 16/0694* (2014.02); *A61M 2202/0208* (2013.01); *A61M 2240/00* (2013.01)

(58) Field of Classification Search
CPC ........... A61M 16/0666–0677; A61M 16/0683; A61M 16/0694; A61M 2240/00; A42B 1/045; A42B 1/24
See application file for complete search history.

(56) References Cited

U.S. PATENT DOCUMENTS

| 4,774,946 A | * | 10/1988 | Ackerman | ........ A61M 16/0633 128/207.18 |
| 4,944,310 A | * | 7/1990 | Sullivan | ............ A61M 16/0683 128/207.18 |
| 5,188,101 A | * | 2/1993 | Tumolo | ............ A61M 16/0633 128/101.1 |

(Continued)

FOREIGN PATENT DOCUMENTS

| EP | 3067085 A1 | | 9/2016 | |
| TW | M536550 | * | 2/2017 | ............ A42B 1/045 |

OTHER PUBLICATIONS

Office Action dated Aug. 22, 2019 of the corresponding Taiwan patent application No. 108105695.

*Primary Examiner* — Valerie L Woodward
(74) *Attorney, Agent, or Firm* — Chun-Ming Shih; HLDS IPR Servives

(57) ABSTRACT

A respirator fixing module applied to a breathing tube includes a cap, a nasal mask structure, a first strap, a second strap, and a third strap. The cap has a first joint; the nasal mask structure has a nasal mask, two first assembling members and a second assembling member extending from the left, the right, and the top sides of the nasal mask respectively, and a communicating pipe and a breathing tube connected to each other; the first strap is installed between the two first assembling members and encircled into a headband; the second strap is connected to the cap, and the second strap has an end surrounding the breathing tube and a second joint adjustably combined with the first joint; and the third strap has an end fixed to the second assembling member and the other end having a third joint adjustably combined with the first joint.

10 Claims, 8 Drawing Sheets

(56) References Cited

U.S. PATENT DOCUMENTS

| | | | |
|---|---|---|---|
| 6,044,844 A | 4/2000 | Kwok et al. | |
| 6,805,117 B1 * | 10/2004 | Ho | A61M 16/0683 128/207.17 |
| 6,889,689 B1 * | 5/2005 | Neuman | A61M 16/0683 128/207.18 |
| 7,575,005 B2 | 8/2009 | Mumford et al. | |
| 2003/0034030 A1 | 2/2003 | Carlucci et al. | |
| 2007/0186931 A1 * | 8/2007 | Zollinger | A61M 16/0683 128/207.11 |
| 2007/0209663 A1 * | 9/2007 | Marque | A61M 16/0616 128/207.11 |
| 2014/0026888 A1 | 1/2014 | Matula, Jr. et al. | |
| 2017/0209656 A1 * | 7/2017 | Linton | A61M 16/0683 |
| 2018/0093060 A1 * | 4/2018 | Lee | A61M 16/0683 |

\* cited by examiner

RESPIRATOR FIXING MODULE

BACKGROUND OF THE INVENTION

1. Technical Field

The technical field relates to a medical mask, and more particularly to a respirator fixing module.

2. Description of Related Art

Continuous Positive Airway Pressure (CPAP) used for Noninvasive Assisted Ventilation (NAV) treatments has long been a widely used method for the treatment of respiratory distress syndromes of premature infants or newborn babies.

Since a poor fixation of CPAP pipe may cause nasal pressure sores easily, and a slippage of the pipe may lead to a poor respiration-assisted function and a prolonged use of the respirators and may result in apnea and bradycardia with hypoxemia conditions of the newborn babies, therefore it is very important to have a comfortable-to-wear and a convenient-to-fix respirator for infants.

However, U.S. Patent Publication No. US2018093060 has disclosed an infant cap for fixing a breathing tube effectively. Although the infant cap can reduce *acnes* effectively, the cap is not fixed to the position of a nasal tube, so that when the infant has intensive activities, the nasal tube may shift or fall off. Since the nasal tube is inserted into an infant's nasal cavity, the infant may feel uncomfortable or even struggle, which in turn may affect the treatment effect.

In addition, the traditional nasal tube design has no possibility of installing or providing a nasogastric tube, and it will be very convenient if we can break through the conventional design and provide two holes for installing both tubes and configured to be corresponsive to a patient's nostrils respectively, and this design provides a convenient way for users to use the nasogastric tube, a channel for installing a sensor that monitors a patient's respiration through the nostrils, an improved convenient monitoring method, or a possibility of feeding the patient.

In view of the aforementioned drawbacks of the prior art, the discloser of this disclosure based on years of experience in the related industry to conduct extensive research and experiment, and finally provided a feasible solution as disclosed in this disclosure to overcome the drawbacks of the prior art.

SUMMARY OF THE INVENTION

Therefore, it is a primary object of this disclosure to overcome the drawbacks of the prior art by providing a respirator fixing module that uses a cap, a first strap, a second strap and a third strap to fix a breathing tube and a nasal mask structure and prevents the breathing tube and the nasal mask from shifting or falling off, and the nasal mask is used to replace the conventional nasal tube and to achieve the effect of a respirator fixing module with the advantage of providing a secured and comfortable wear.

To achieve the aforementioned and other objectives, this disclosure discloses an embodiment of a respirator fixing module applied to a breathing tube. The respirator fixing module comprises: a cap, having a first joint; a nasal mask structure, having a nasal mask, two first assembling members extending from both left and right sides of the nasal mask respectively, and a second assembling member extending from the upper side of the nasal mask, and the nasal mask further having a communicating pipe extending therefrom and coupled to the breathing tube; a first strap, installed between the two first assembling members and encircled into a headband; a second strap, coupled to the cap, and having an end sheathed on the breathing tube, and a second joint adjustably combined with the first joint; and a third strap, having an end fixed to the second assembling member and the other end having a third joint adjustably combined with the first joint.

Wherein, both sides of the nasal mask are positioned by the first strap, and the breathing tube is positioned by the second strap and the cap, and the cap and the nasal mask are positioned by the third strap, so that the respirator fixing module has a plurality of fixing points to prevent an infant from getting rid of the breathing tube and the nasal mask. If the breathing tube comes with a quantity of two, then the respirator fixing module of this disclosure has a five-point fixing effect including two fixing points at both ends of a user's nose, two fixing points at two side pipes, and one fixing point at the user's forehead to substitute the three-point fixing effect of the conventional nasal tube.

Wherein, the design of the nasal mask includes a breakthrough of the easily manufactured nasogastric holes which are configured to be corresponsive to a patient's nostrils to provide a convenient channel for the patient to use the nasogastric tube or to install a sensor for monitoring the patient's respiration through the nostrils, so that the respirator fixing module has both convenient monitoring and feeding functions.

DESCRIPTION OF THE PREFERRED EMBODIMENTS

Figure 1:
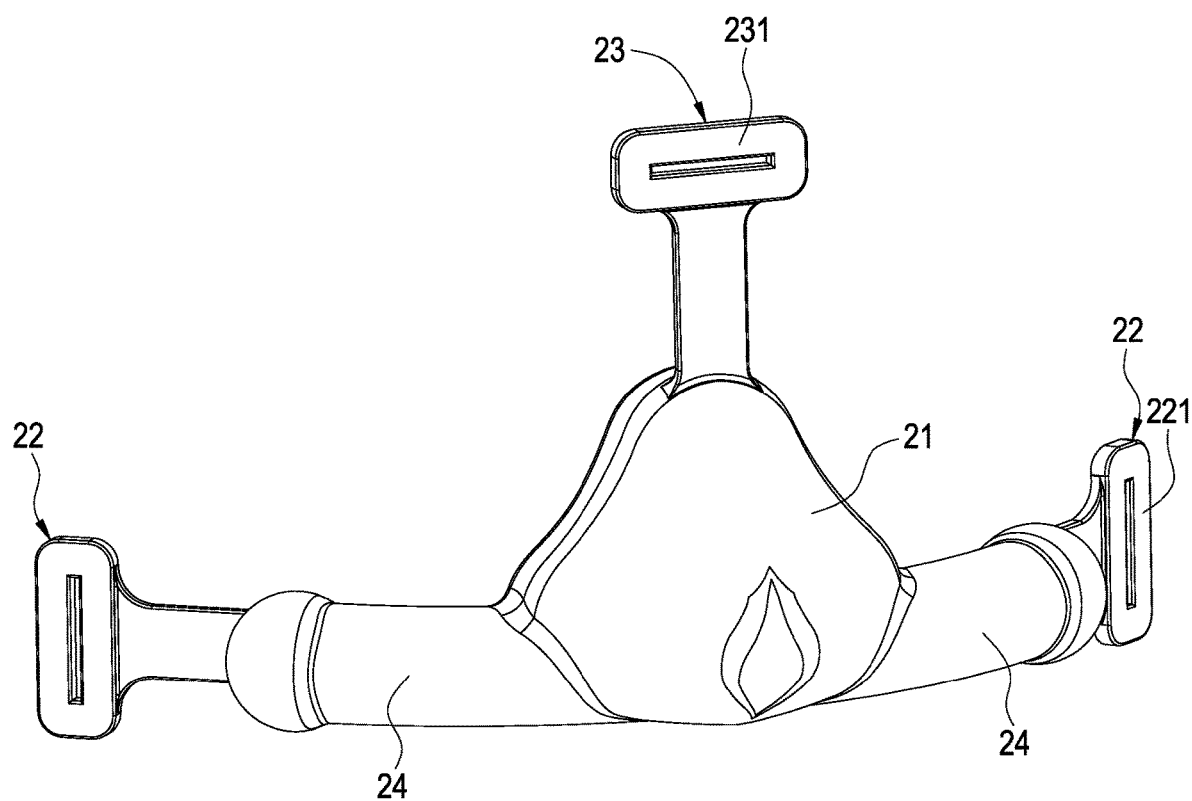
FIG. 1 is a perspective view of a nasal mask structure of this disclosure.

The technical contents of this disclosure will become apparent with the detailed description of preferred embodiments accompanied with the illustration of related drawings as follows. It is intended that the embodiments and drawings disclosed herein are to be considered illustrative rather than restrictive.

With reference to FIGS. 1 to 8 for a respirator fixing module of this disclosure, the respirator fixing module is applied to one or more breathing tubes 100, and the respirator fixing module 10 comprises a cap 1, a nasal mask structure 2, a first strap 3, a second strap 4 and a third strap 5.

Figure 5:
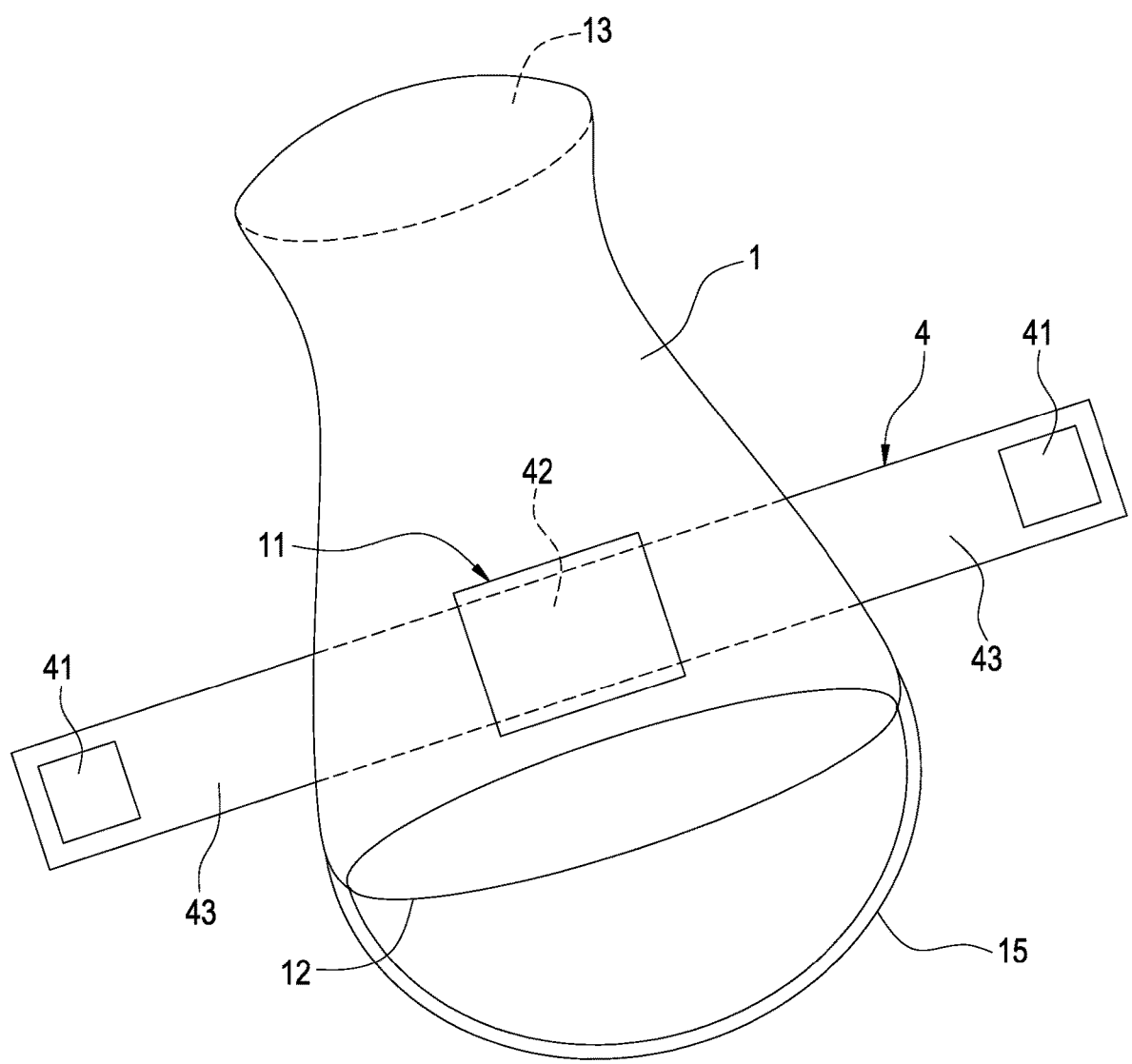
FIG. 5 is a schematic view showing the assembly of a cap and a first fixing strap of this disclosure.
Figure 6:
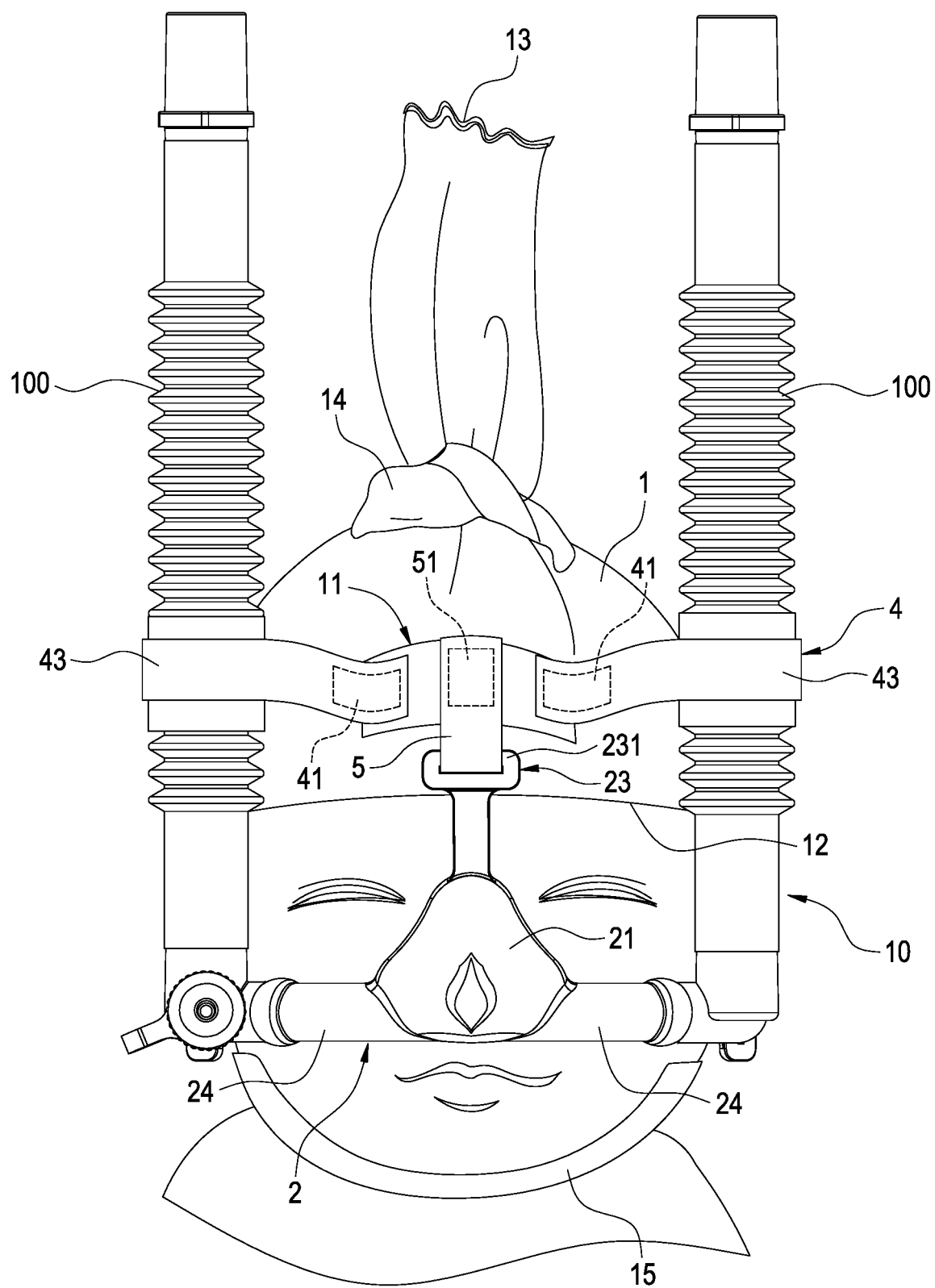
FIG. 6 is a schematic view showing a using status of a respirator fixing module of this disclosure.

In FIGS. 5 and 6, the cap 1 has a first joint 11 further including a first sheath opening 12, a second sheath opening 13, and a tightening part 14 installed between the first sheath opening 12 and the second sheath opening 13, and the cap 1 has a peripheral size tapering in a direction from the first sheath opening 12 to the second sheath opening 13 to facilitate wearing the respirator to the infant's head, and the tightening part 14 may be disposed at the knotted position of the cap 1 (as shown in FIG. 6) or may be an elastic band (not shown in the figure), and the cap 1 is capable of covering the entire head of the infant while exposing the infant's face only, and the upper edge of the cap 1 can be tightened selectively and appropriately by the tightening part 14 to prevent the cap 1 from falling off or sliding down from the infant's head, and thus improving the comfort of wearing and maintaining the infant's head warm.

In addition, the cap 1 has a chin strap 15 extending from the opening peripheral edge of the first sheath opening 12, and the chin strap 15 further fixes the cap 1 to the infant's head and also assists the infant to shut his/her mouth to prevent oxygen from leaking from his/her mouth to achieve an effective treatment effect.

In addition, the cap 1 is better used as a cap for infants, newborns, babies, or young children, and the cap 1 is preferably made of a wool woven fabric, a knitted fabric, or any other suitable fabric compositions, so that the cap 1 has a specific elasticity. However, this disclosure is not limited to such arrangement only.

In FIGS. 1 to 4 and 6 to 8, the nasal mask structure 2 comprises a nasal mask 21, two first assembling members 22 extending from both left and right sides of the nasal mask 21 respectively, and a second assembling member 23 extending from an upper side of the nasal mask 21, and each first assembling member 22 is a first loop 221, and the second assembling member 23 is a second loop 231, and the nasal mask 21 further has one or more communicating pipes 24, extending therefrom and coupled to the breathing tube 100, so that oxygen can enter into the nasal mask 21 through the breathing tube 100 to facilitate the infant to inhale the oxygen gas through the nose.

In the breathing tube 100 of this embodiment, there are two communicating pipes 24, and each communicating pipe 24 is coupled to each respective breathing tube 100, but the quantity of the communicating pipes 24 and the quantity of the breathing tubes 100 may be adjusted according to the method of connection, but are not limited by this embodiment.

Figure 4:
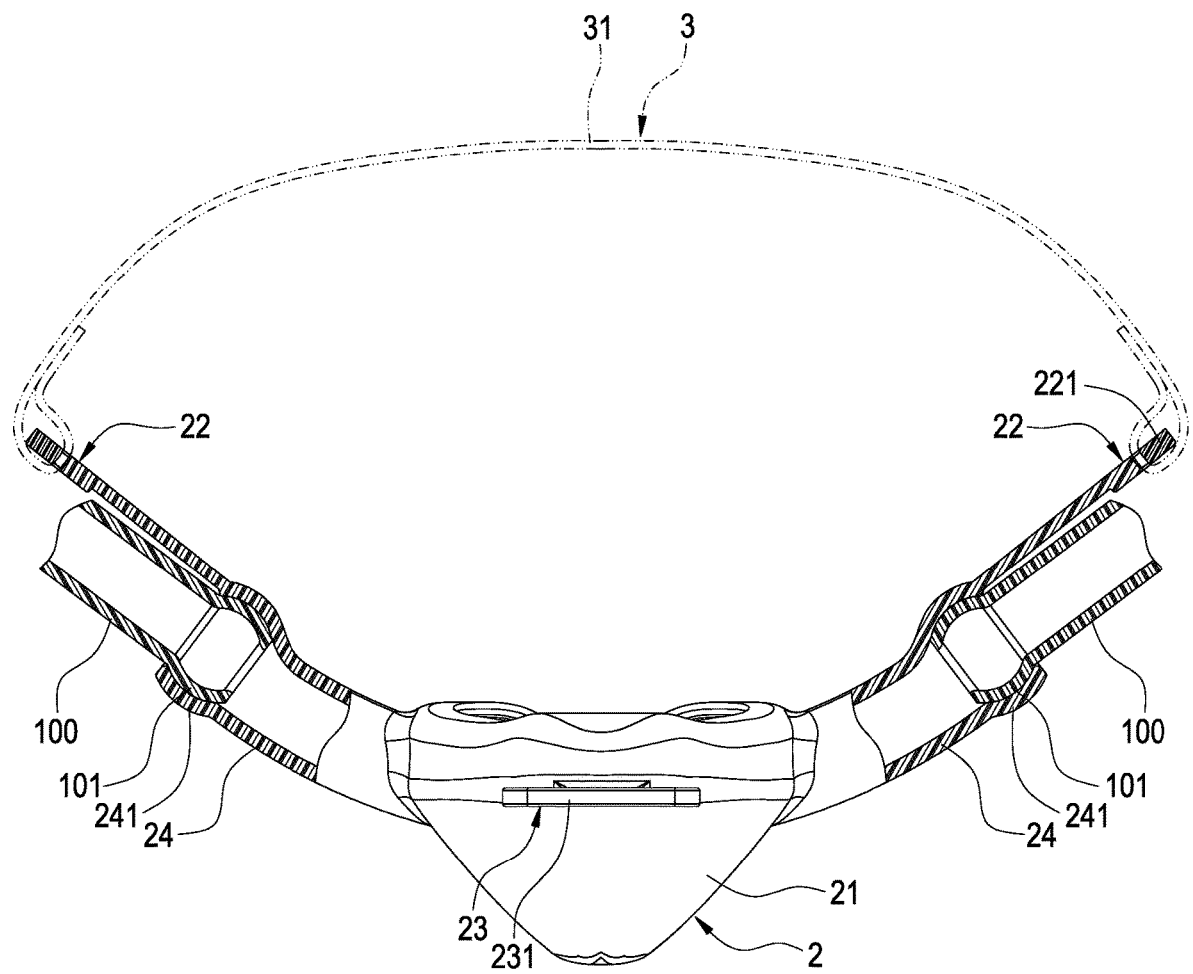
FIG. 4 is a cross-sectional view of a respirator fixing module of this disclosure.

In FIG. 4, the communicating pipe 24 has an arcuate connector 241 at an end thereof, and the breathing tube 100 has an arcuate end 101 at an end thereof, and each arcuate end 101 is passed and coupled into each respective arcuate connector 241 to facilitate the installation of the breathing tube 100 and the communicating pipe 24 and resist the pulling force between the breathing tube 100 and the communicating pipe 24.

Figure 3:
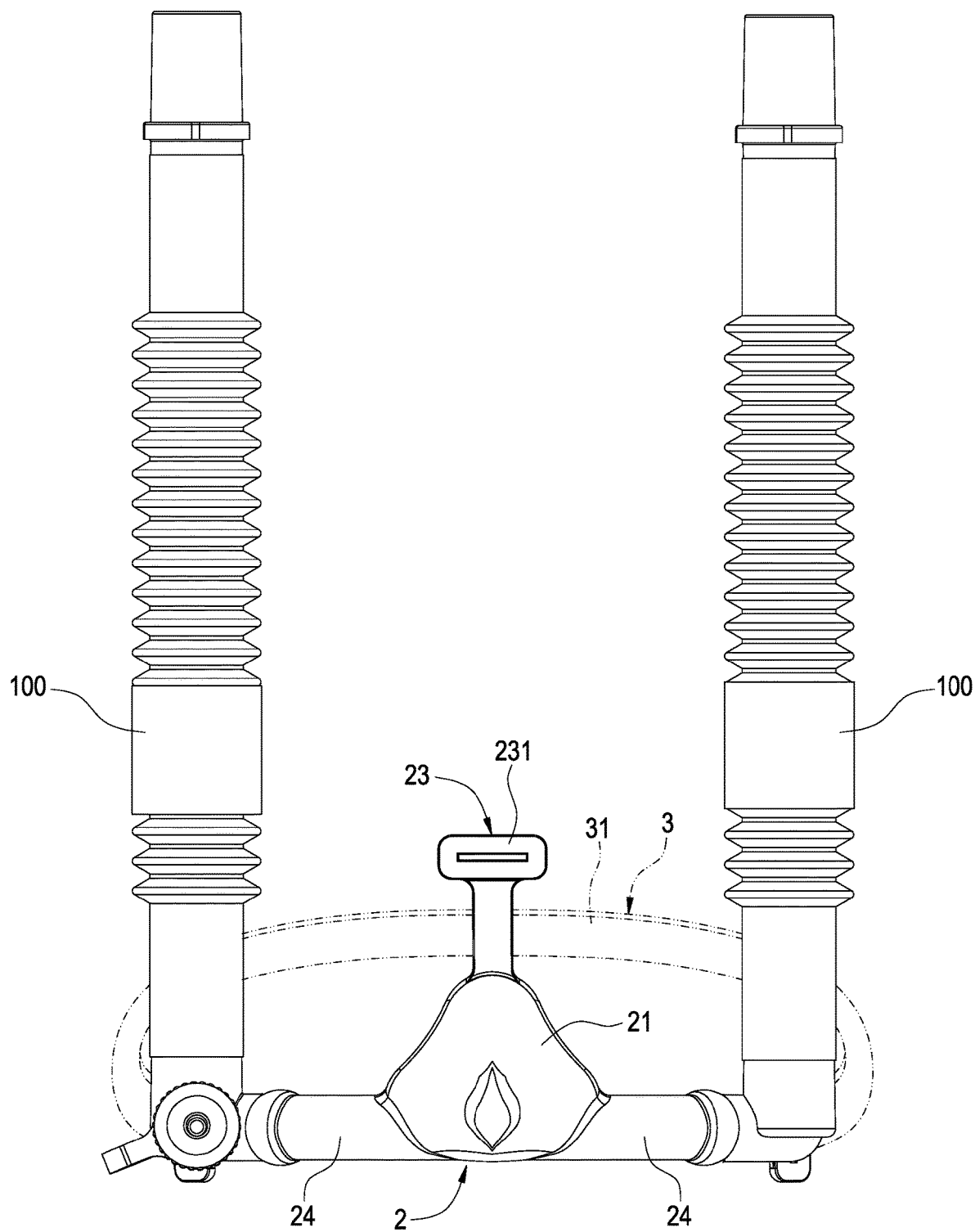
FIG. 3 is a front view of a respirator fixing module of this disclosure.

In FIGS. 3 and 4, both ends of the first strap 3 are sheathed and coupled to each first loop 221, so that the first strap 3 can be installed between two first assembling members 22 and encircled into a headband 31, wherein the headband 31 roughly surrounds the infant's head from the ear of the infant to the back of the head of the infant.

In FIGS. 5 and 6, the second strap 4 is coupled to the cap 1 and disposed between the first sheath opening 12 and the tightening part 14, and an end of second strap 4 is sheathed on the breathing tube 100 and has a second joint 41.

Specifically, the breathing tube 100, the communicating pipe 24, and the second joint 41 of this embodiment come with a quantity of two each, and the second strap 4 has a middle section 42, and two side sections 43 disposed on both sides of the middle section 42 respectively, and the middle section 42 is fixed to the back side of the cap 1, and the first joint 11 is fixed to the front side of the cap 1, and each side section 43 is folded and sheathed on each respective breathing tube 100, and each second joint 41 is fixed to an end of each respective side section 43 and adjustably combined with the first joint 11.

Wherein, the first joint 11 and the second joint 41 are Velcro tapes, adhesive tapes, male-and-female buckles or mother-and-child buckles coupled to each other, and the interval between the breathing tube 100 and the cap 1 according to the attaching position of the Velcro tapes or adhesive tapes. Similarly, the quantity of the fasteners such as the male-and-female buckles and mother-and-child buckles can be increased to adjust the interval between the breathing tube 100 and the cap 1 according to the buckling position, so as to achieve the effect of adjustably combining the second joint 41 with the first joint 11.

In FIG. 6, an end of the third strap 5 is sheathed on and coupled to the second loop 231, so that an end of the third strap 5 is fixed to the second assembling member 23 and the other end of the third strap 5 has a third joint 51 adjustably combined with the first joint 11.

Wherein, the first joint 11 and the third joint 51 are Velcro tapes, adhesive tapes, male-and-female buckles or mother-and-child buckles coupled to each other, and the interval between the nasal mask 21 and the cap 1 can be adjusted according to the attaching positions of the Velcro tapes or adhesive tapes. Similarly, the quantity of male-and-female buckles and the quantity of mother-and-child buckles can be increased to adjust the interval between the nasal mask 21 and the cap 1 according to the buckling position to achieve the effect of adjustably combining the third joint 51 with the first joint 11.

In addition, the first strap 3, the second strap 4, and the third strap 5 are elastic bands, PBT elastic bands, cotton gauze woven bands, or any other appropriate elastic bands which come with various sizes to fit different infants' heads.

Figure 2:
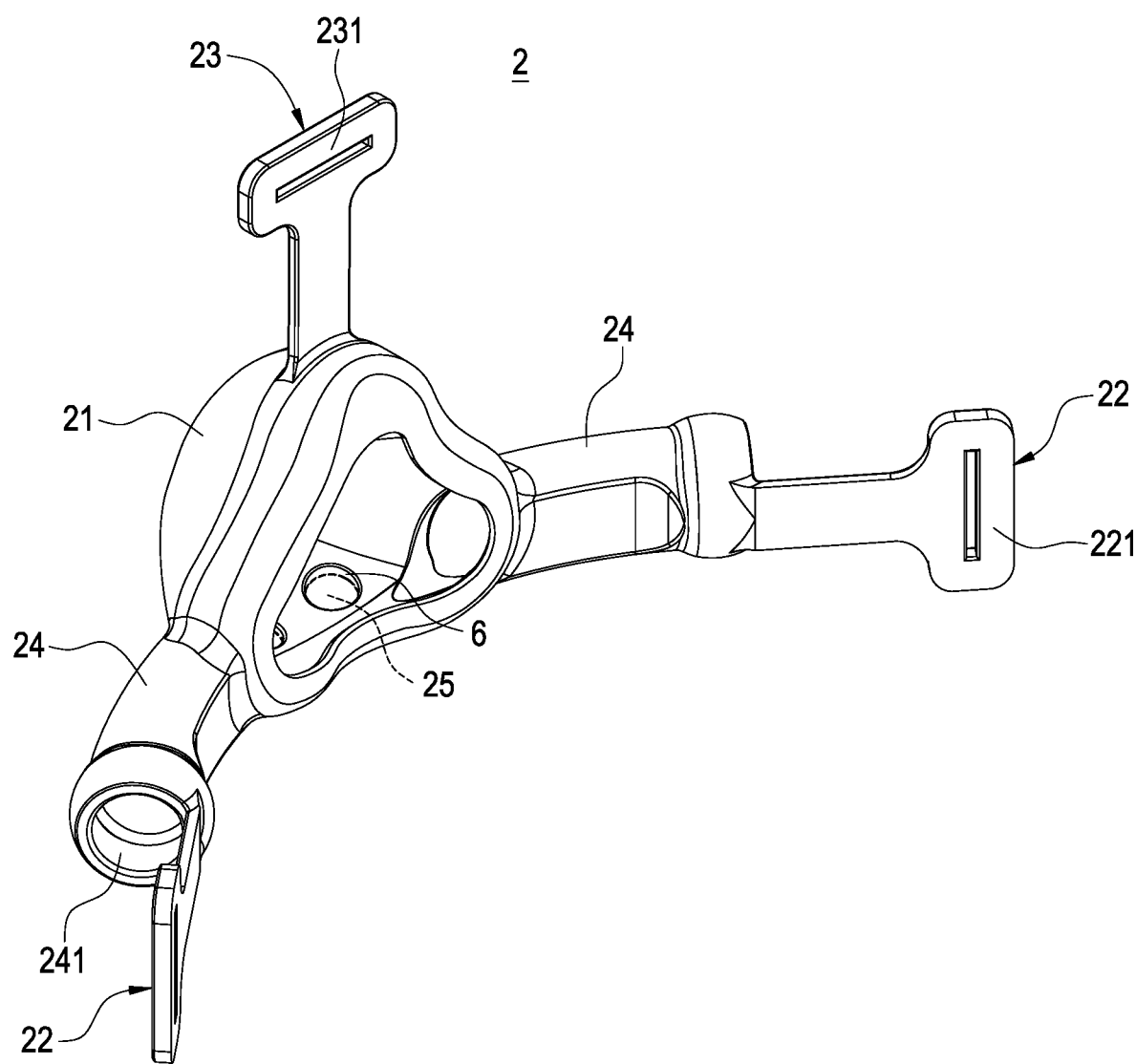
FIG. 2 is another perspective view of a nasal mask structure of this disclosure.
Figure 7:
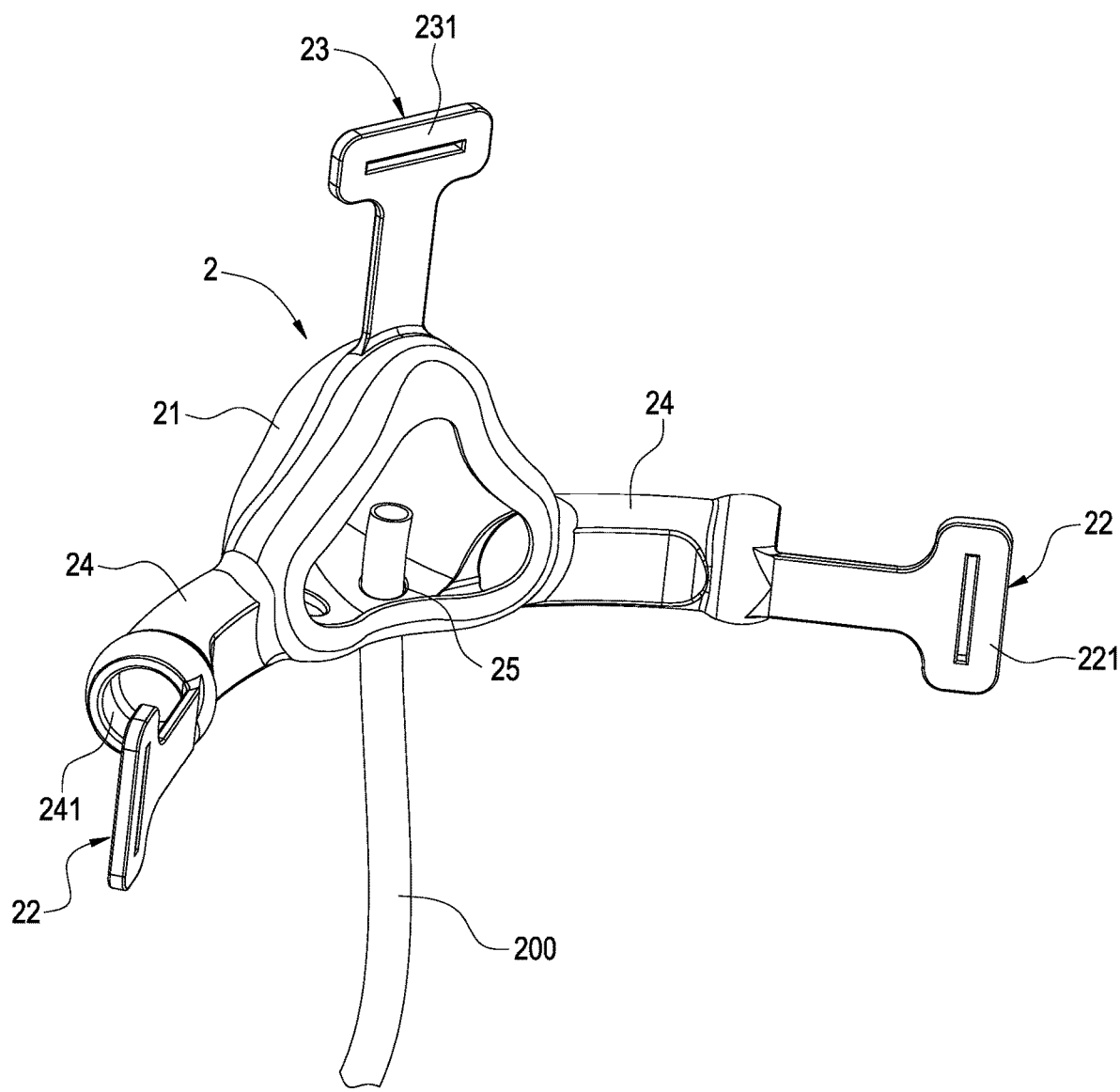
FIG. 7 is a schematic view showing another using status of a respirator fixing module of this disclosure.
Figure 8:
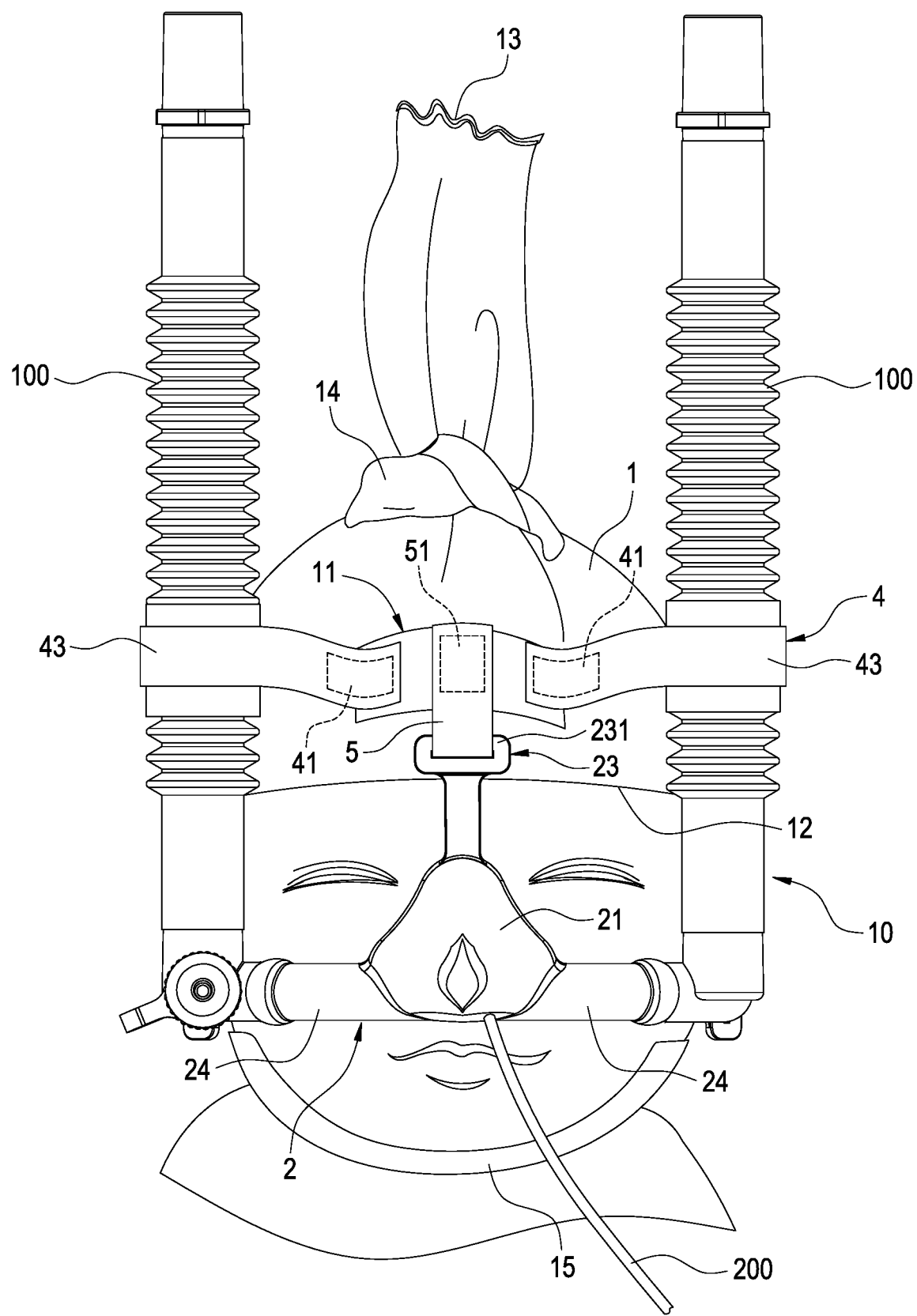
FIG. 8 is a schematic view showing a further using status of a respirator fixing module of this disclosure.

In FIGS. 2, 7, and 8, the respirator fixing module 10 of this disclosure further comprises one or more covers 6, and the nasal mask 21 has one or more nasogastric holes 25. When an infant cannot be fed normally, the nasogastric holes 25 are provided for installing the nasogastric tubes 200 to assist the infant to his/her eating through the nasal tube, and the cover 6 detachably covers the nasogastric holes 25.

In addition, the conventional nasal tube 1 is not designed with the nasogastric tube, and the design of the nasal mask 21 of this embodiment has two easily manufactured nasogastric holes 25 configured to be corresponsive to the patient's nostrils respectively to provide a way for users to use the nasogastric tube 200 and a convenient channel for installing a sensor that monitors a patient's respiration through the nostrils, so that the respirator fixing module 10 has both convenient monitoring and feeding functions.

With reference to FIGS. 3 to 6 for the using statuses of a respirator fixing module 10 of this disclosure, the first strap 3 is provided for mounting the nasal mask 21 onto an infant's nose, and then the cap 1 is worn on the infant's head, and the second strap 4 is used to fix the breathing tube 100 to both left and right sides of the cap 1, or the breathing tube 100 is fixed onto the cap 1 by the second strap 4 first, and then the cap 1 is worn on the infant's head, and changes or adjustments are made according to different conditions and requirements, and finally an end of the third strap 5 is fixed to the cap 1 and the other end of the third strap 5 is fixed to the nasal mask 21. Therefore, the cap 1, the first strap 3, the second strap 4 and the third strap 5 can fix the breathing tube 100 and the nasal mask structure 2 effectively to prevent the breathing tube 100 and the nasal mask 21 from shifting or falling off. The cap 1 is applicable of the head circumferences of different infants, and the nasal mask 21 substitutes the conventional nasal tube to achieve the effect that the respirator fixing module 10 has the advantage of stable and comfortable wearing and provide a convenient use for newborns, babies, and young children.

In addition, both left and right sides of the nasal mask 21 are fixed by the first strap 3, and the breathing tube 100 is fixed to the cap 1 by the second strap 4, and the cap 1 and the nasal mask 21 are fixed by the third strap 5, so that the respirator fixing module 10 has a plurality of fixing points to prevent the infant from getting rid of the breathing tube 100 and the nasal mask 21. If there are two breathing tubes 100, then the respirator fixing module 10 of this disclosure has a the five-point fixing effect including two fixing points at the nose, two fixing points at the two side pipes, and one fixing point at the user's forehead to replace the three-fixing point effect of the conventional nasal tube.

In FIG. 2, the surface of the nasal mask 21 and the communicating pipe 24 of this disclosure attached onto the user's face is designed as a curved surface, since the surface of the nasal mask 21 and the surface of the communicating pipe 24 have a certain curvature for shifting the fixed gravity downward, so that when the user wears the nasal mask 21 and the communicating pipe 24, the nasal mask 21 and the communicating pipe 24 can attach and fit the human curve better to improve the comfortability and stability of using the respirator fixing module 10.

In summation of the description above, this disclosure complies with patent application requirements, and thus is duly filed for patent application. While this disclosure has been described by means of specific embodiments, numerous modifications and variations could be made thereto by those skilled in the art without departing from the scope and spirit of this disclosure set forth in the claims.

What is claimed is:

1. A respirator fixing module, comprising:
   two breathing tubes;
   a cap, having a first joint;
   a nasal mask structure, having a nasal mask, two communicating pipes extending from both left and right sides of the nasal mask and coupled to the two breathing tubes respectively, two first assembling members extending from the two communicating pipes, respectively, and a second assembling member extending from an upper side of the nasal mask;
   a first strap, installed between the two first assembling members and encircled into a headband;
   a second strap, coupled to the cap, and having two ends surrounding the two breathing tubes respectively, and two second joints respectively at the two ends adjustably combined with the first joint; and
   a third strap, having an end fixed to the second assembling member and the other end having a third joint adjustably combined with the first joint.

2. The respirator fixing module of claim 1, the second strap has a middle section and two side sections disposed on both sides of the middle section respectively, and the middle section is fixed to a back side of the cap, and each side section is sheathed on a respective breathing tube, and each second joint is fixed to an end of each respective side section to be adjustably combined with the first joint that is fixed to a front side of the cap.

3. The respirator fixing module of claim 2, wherein the first joint and the two second joints are adhesive tapes, male-and-female buckles or mother-and-child buckles coupled to each other, and the first joint and the third joint are adhesive tapes, male-and-female buckles or mother-and-child buckles coupled to each other.

4. The respirator fixing module of claim 1, wherein the cap has a first sheath opening, a second sheath opening and a tightening part installed between the first sheath opening and the second sheath opening.

5. The respirator fixing module of claim 4, wherein the cap has a peripheral size tapering in a direction from the first sheath opening to the second sheath opening.

6. The respirator fixing module of claim 4, wherein the second strap is installed between the first sheath opening and the tightening part.

7. The respirator fixing module of claim 4, wherein the cap has a chin strap extending from a peripheral edge of the first sheath opening, and the cap is made of a wool woven fabric or a knitted fabric.

8. The respirator fixing module of claim 1, further comprising at least one cover, and the nasal mask having at least one nasogastric hole, and the cover detachably covering the nasogastric hole.

9. The respirator fixing module of claim 1, wherein each communicating pipe has an arcuate connector installed at an end thereof.

10. The respirator fixing module of claim 1, wherein each first assembling member is a first loop, and both ends of the first strap are sheathed on and coupled to the first loops respectively, and the second assembling member is a second loop, and an end of the third strap is sheathed on and coupled to the second loop.

* * * * *